(12) United States Patent
Osborn, III et al.

(10) Patent No.: US 6,358,235 B1
(45) Date of Patent: *Mar. 19, 2002

(54) SOFT CONFORMABLE HOLLOW BAG TAMPON

(75) Inventors: Thomas Ward Osborn, III; Jerry Edward Carstens; Kimberly Ann Buck; Lisa Ann MacKay; Ronald Bosman Visscher, all of Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/177,221

(22) Filed: Oct. 22, 1998

Related U.S. Application Data

(63) Continuation-in-part of application No. 09/124,407, filed on Jul. 29, 1998, and a continuation-in-part of application No. 09/124,351, filed on Jul. 29, 1998, now Pat. No. 6,095,998.

(51) Int. Cl.[7] .................................................. A61F 13/15
(52) U.S. Cl. .................................. 604/385.18; 604/904
(58) Field of Search ................................ 604/904, 363, 604/385.1, 286, 330, 385.17, 385.18

(56) References Cited

U.S. PATENT DOCUMENTS

| | | | |
|---|---|---|---|
| 61,417 A | 2/1867 | Grant | |
| 1,884,089 A | * 10/1932 | Millner | ......................... 604/904 |
| 1,969,671 A | 8/1934 | Nelson | |
| 2,330,257 A | * 9/1943 | Bailey | ......................... 604/904 |
| 2,458,685 A | 1/1949 | Crockford | |
| 2,607,346 A | 8/1952 | Milcent | |
| 2,733,714 A | 2/1956 | Haas | |
| 2,884,925 A | 5/1959 | Meynier, Jr. | |
| 3,068,867 A | 12/1962 | Bletzinger et al. | |
| 3,495,586 A | 2/1970 | Regenbogen | |
| 3,706,311 A | 12/1972 | Kokx et al. | |
| 3,712,305 A | * 1/1973 | Wennerblom et al. | ...... 604/904 |
| 3,749,094 A | 7/1973 | Duncan | |
| 3,753,437 A | 8/1973 | Hood et al. | |
| 3,762,413 A | 10/1973 | Hanke | |
| 3,834,389 A | * 9/1974 | Dulle | ......................... 604/904 |
| 3,856,013 A | * 12/1974 | Dulle | ......................... 604/904 |
| 3,857,395 A | 12/1974 | Johnson et al. | |
| 3,971,398 A | 7/1976 | Krantz | |
| 3,983,868 A | 10/1976 | Ring | |

(List continued on next page.)

Primary Examiner—Dennis Ruhl
(74) Attorney, Agent, or Firm—Matthew P. Fitzpatrick; Ingrid N. Hickman; Kevin C. Johnson

(57) ABSTRACT

A catamenial tampon in the form of a soft, conformable, hollow bag which is disclosed. The tampon is capable of being inserted digitally or through the use of a unique applicator. The tampon preferably comprises a removal string, which can be attached to the inside or outside surface of the tampon. In one embodiment, the removal string is attached to the inside surface of the tampon, adjacent to the head of the tampon to facilitate inversion of the tampon upon removal. The tampon may have a cross-section in which two of its sides are pleated, allowing the sides of the tampon to expand laterally. The tampon may be provided with a plurality of pleats disposed around its cross-section that are capable of opening in any desired direction. The outside surface of the tampon may be smooth, or it can be textured. In a textured embodiment, the tampon may have an outside surface which comprises microfibrils or other texturing elements extending outwardly therefrom. These may be randomly oriented or may be aligned in a particular direction or directions. The tampon may also be provided with an annular ring which assists it in contacting the vaginal surfaces, and may also be constructed such that it is generally cylindrical or circular in cross-section, without a major surface. A feature such as this allows the tampon to be inserted in any orientation without losing its ability to expand effectively in the lateral direction once inserted.

14 Claims, 8 Drawing Sheets

U.S. PATENT DOCUMENTS

| | | |
|---|---|---|
| 3,986,511 A | 10/1976 | Olofsson et al. |
| 4,018,225 A * | 4/1977 | Elmi .......................... 604/904 |
| 4,211,225 A | 7/1980 | Sibalis |
| 4,212,301 A * | 7/1980 | Johnson ...................... 604/904 |
| 4,271,835 A | 6/1981 | Conn et al. |
| 4,536,178 A | 8/1985 | Lichstein et al. |
| 5,346,468 A | 9/1994 | Campion et al. |
| 5,370,633 A | 12/1994 | Villata |
| 5,558,631 A | 9/1996 | Campion et al. |
| 5,659,934 A | 8/1997 | Jessup et al. |

* cited by examiner

SOFT CONFORMABLE HOLLOW BAG TAMPON

CROSS REFERENCE TO RELATED APPLICATIONS

This is a continuation in part of Ser. No. 09/124,407 and a continuation in part of Ser. No. 09/124,351 now U.S. Pat. No. 6,095,998 both filed on Jul. 29, 1998.

FIELD OF THE INVENTION

This invention relates to catamenial tampons, and more particularly to an improved tampon which is in the form of a soft, conformable, hollow bag and which covers a substantial portion of the interior of the vaginal cavity.

BACKGROUND OF THE INVENTION

It has been long recognized that the internal vaginal cavity in its normal collapsed state is of much wider dimension in its transverse plane than in its vertical plane. It is equally well known that the minimum dimension of the vagina is near the introitus while the maximum dimension is near the cervix. It is desirable, therefore, when considering a tampon for catamenial use, to provide a structure which is in its initial state is of a size small enough to pass through the vaginal orifice without discomfort, and when once inside the vaginal cavity and beyond the restrictions of the orifice may be expanded, particularly in the lateral direction, to contact substantially all of surface of the vaginal walls from one side to the other in the vaginal cavity to prevent early bypass of the menstrual discharges from the cervix. Since the vaginal wall in its normal collapsed state is flaccid and has multiple folds and wrinkles which provide channels through which a significant portion of the menstrual fluids normally flow, it is also important that the absorbent tampon be as soft and conformable as possible, in order to conform to shape of the vaginal cavity and fit within these channels to minimize leakage.

The absorbent catamenial tampons now in general use comprise small, highly compressed, cylindrical plugs about three-eighths to one-half inch (about 1.0 cm to 1.3 cm) in diameter and from 1½ to 2½ inches in length (about 3.8 cm to 6.4 cm). Because of the need for absorbent capacity, they are usually formed from batts much larger in size than the vaginal orifice, and compressed to the small size indicated above in order to facilitate insertion. As fluid is absorbed, these compressed tampons are expected to re-expand toward their original pre-compressed size, and to eventually become large enough to effectively cover the vaginal cavity against fluid leakage or bypass. While it has been found that these compressed tampons perform their intended function tolerably well, even the best of them do not re-expand sufficiently, or fast enough, to provide good transverse coverage against leakage even though the vertical block may be satisfactory. Further, most of these tampons often use only a small portion of their absorptive capacity before leakage. Since these tampons require some fluid absorption to re-expand, it is clear that fluid bypass and leakage can occur prematurely, and can particularly occur immediately following the time of insertion.

Numerous attempts have been made to solve this problem with some approaches focusing on the applicator and others focusing on the tampon itself.

For example, some approaches in the patent art suggest a tampon with a built-in mechanical expansion means, a typical example being U.S. Pat. No. 3,706,311 to Kohx et al. However, while a good transverse block appears to be produced, the mechanical expansion means disclosed in that patent is in the form of a flat springlike element which after insertion permanently maintains the spread configuration of the tampon, may make it difficult to remove.

Another approach is described in U.S. Pat. No. 3,512,528 to Whitehead et al, which teaches the use of a sack of absorbent material collapsed to a small size for insertion and which after insertion is expanded by the introduction of a gas or a fluid internally of the sack. The multiple steps and complicated manipulation of the gas or fluid introduction means required when using this type of tampon detract from what otherwise appears to be an effective solution of the problem.

Still another approach is described in U.S. Pat. No. 3,857,395 issued to Johnson, et al. The Johnson, et al. patent teaches the use of an elongated inserter device over which a flat tampon is draped. The inserter is said to permit the draped portion of the tampon to be pulled, rather than pushed into the cavity from the point at which the tampon is supported on the leading end of the inserter. The inserter means is equipped with a bilateral expansion mechanism which at the user's option may be operated to transversely spread the tampon at the time of insertion. The inserter device described in the Johnson, et al. patent suffers from many drawbacks, however. The Johnson inserter device is a complicated device comprising a pair of hinged arms that are capable of laterally diverging at a hinge or joint. The angular nature of the hinged arms would make that inserter uncomfortable to use. The complex nature of the hinged arms would also make it difficult and expensive to manufacture. As a result, it would not be suitable as a disposable applicator.

Another problem that exists in deploying tampons having a greater transverse dimension within the vaginal cavity is that this greater transverse dimension of the vaginal cavity is roughly perpendicular to the vaginal opening.

One attempt to address this latter problem is described in U.S. Pat. No. 3,068,867 issued to Bletzinger, et al. The Bletzinger, et al. patent is directed to a tampon insertion device having a positioning indicator thereon. The device described in the Bletzinger, et al. patent comprises an insertion device for tampons which are either of cylindrical cross-section, or non-cylindrical cross-section but constructed to expand when subjected to fluids in a non-cylindrical shape. The insertion device is provided with an indicator that aids the user in inserting the tampon with its major cross-sectional axis transverse to the major axis of the vaginal opening. The Bletzinger device, however, is awkward in that it requires insertion of the widest dimension of the tampon cross-wise to the narrowest dimension of the vaginal opening.

Another series of attempts to overcome the problems associated with conventional, highly compressed, fluid expanding tampons is described in U.S. Pat. No. 3,749,094 issued to Duncan and U.S. Pat. Nos. 3,794,029 and 3,766,921 both issued to Dulle. The Duncan and Dulle devices are all generally conical and are designed to be dry-expanding. While these devices would be expected to overcome some of the problems associated with highly compressed, fluid expanding tampons, the Duncan and Dulle devices still require significant rigidity and compression in order to permit their use in a conventional "tube and plunger" type applicator for which they are designed.

It has been found during development of the present invention that a tampon constructed according to the invention described herein can provide even further improvements in comfort, low wearing awareness, and performance as compared to currently marketed tampons and previous attempts to improve upon such tampons such as those described above. Tampons according to the present invention may be designed for digital insertion. Alternatively, a unique tampon applicator which is capable of effectively deploying a tampon of the type described herein may also be provided.

SUMMARY OF THE INVENTION

This invention relates to catamenial tampons, and more particularly to an improved tampon which is in the form of a soft, conformable, hollow bag and which covers a substantial portion of the interior of the vaginal cavity.

In one embodiment, the tampon of the present invention, has a bag-like conformable absorbent body. The tampon has an outer surface, an inner surface, a head portion and a trailing portion. The inner surface of the tampon defines an interior of the tampon wherein the head portion is closed and the trailing portion defines an opening into the interior of the tampon. The tampon may have a shape modulus of compression of less than 0.05 pounds force. The tampon may also comprise a withdrawal sting attached to the absorbent party of the tampon. The withdrawal string may be attached to the head portion of the absorbent body. The string may also be disposed within the interior of the tampon. In some preferred embodiments, the string may be attached to the head portion of the tampon and a portion of the string may be disposed within the interior of the tampon such that the tampon is inverted when the withdrawal sting is pulled for removal.

In one embodiment, the tampon comprises an absorbent material selected from the group consisting of: rayon, cotton, superabsorbent material, and blends thereof.

In another embodiment, the outer surface of the tampon may comprise texturing elements. The texturing elements in one preferred embodiment comprise texturing fibers. The texturing elements may be hydrophilic. The texturing elements may comprise capillary channel fibers. Additionally, the texturing elements may have a lower density than the outer surface of said tampon such that a density gradient is created from the texturing elements to the outer surface of the tampon.

In another embodiment, the tampon comprises at least one pleated fold in said outer surface. The tampon may comprise a pair of pleats located at opposite sides of said outer surface.

In one embodiment, the tampon may comprises a layered structure such that the material composition of the outer surface of the tampon differs from the material composition or density of the inner surface of the tampon. The tampon may comprise at least an outer layer and an inner layer wherein at least a portion of the outer layer defines the outer surface and wherein at least a portion of the inner layer defines the inner surface. The inner surface may comprises a liquid impervious barrier. The inner layer of the tampon may have a higher density than the outer layer. The inner layer may comprise primarily cotton. The outer layer may comprises primarily rayon.

In one embodiment of the tampon of the present invention, when the tampon is compressed in a flat configuration the outer surface has a maximum width which exceeds the width of the opening of the trailing portion of the tampon. The tampon may have a plan view when collapsed which is generally balloon-shaped. The tampon may have a syngyna absorbency of from about 5 to about 30 grams.

DETAILED DESCRIPTION OF THE INVENTION

This invention relates to catamenial tampons, and more particularly to an improved tampon which is in the form of a soft, conformable, hollow bag and which covers a substantial portion of the interior of the vaginal cavity.

Figure 1:
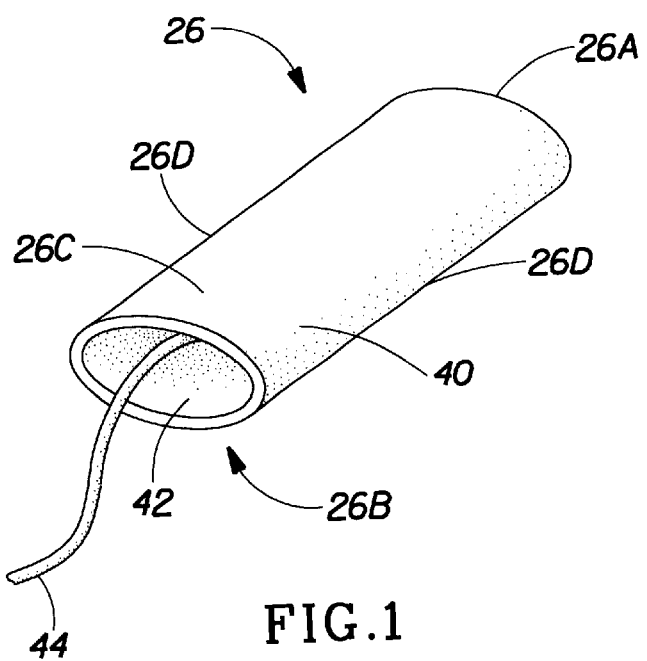
FIG. 1 is a perspective view of a tampon of the present invention.

The tampon of the present invention is designed to achieve maximum fit (side-to-side coverage of the vaginal surface area) without significant distortion of the vaginal surface. FIG. 1 shows one embodiment of the tampon of the present invention, tampon 26. As shown in FIG. 1, the tampon 26 is generally shaped like a hollow bag or an inverted sock (that is, a shape like the portion of a sock that is worn on a wearer's foot, not including the angled portion that is worn over the wearer's ankle).

The tampon 26 has a head 26A or end that is the first portion of the tampon 26 to be inserted into the vaginal cavity, a trailing end 26B, surfaces 26C, and edges 26D. The tampon 26 is "bag like" or "bag shaped" in that it preferably has an open trailing end 26B, and a hollow, rather than a solid interior. Thus, the tampon 26 preferably has two or more surfaces (or sides) 26C that are joined together, a closed head end 26A, and an open trailing end 26B.

The tampon 26 is preferably highly flaccid and conformable to the body such that it compensates for and responds to body movements. The tampon 26 need not be, and preferably is not pre-compressed to a point where the fibers temporarily "set" and re-expand upon the absorption of fluid. Because the tampon 26 may be designed for digital insertion or insertion with a unique applicator, it need not rely on resiliency or "spring" within the fibers of the tampon itself to re-expand. This feature allows the tampon 26 to be significantly more flaccid and conformable than previous tampons and, consequently, more comfortable and effective for fluid acquisition than such devices.

Figure 2:
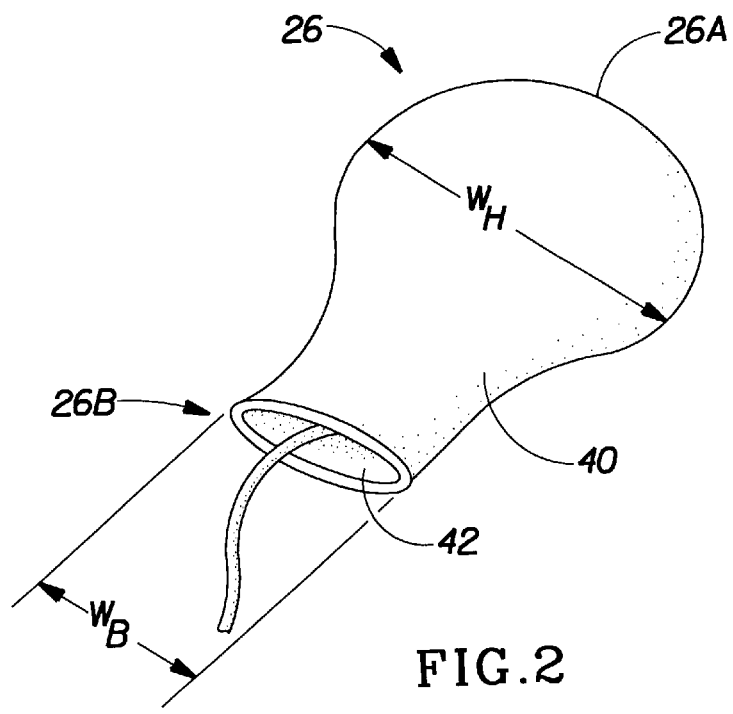
FIG. 2 is a perspective view of an additional embodiment of the tampon of the present invention.

The size and shape of the tampon 26 is important to its comfort and effectiveness. As described, the tampon 26 preferably has a hollow interior and can be configured in a wide variety of shapes such as a shape generally resembling an "oven mitt" without the thumb portion or a "sock" without the ankle portion. The tampon 26 preferably has a generally flat configuration when deployed which allows it to conform to the shape of the vaginal cavity. (The shape of the vaginal cavity is described in greater detail in U.S. Pat. No. 3,749,094 issued to Duncan on Jul. 31, 1973.) The tampon 26 may have a number of suitable plan view shapes. Suitable plan view shapes, include, but are not limited to: generally rectangular with rounded edges, generally trapezoidal, conical, or as shown in FIG. 2, a shape that resembles an oven mitt (without the thumb portion). The tampon 26 can be of any suitable size. The tampon 26 shown in FIG. 1 preferably has a length measured from the head 26A to the trailing end 26B in the range of about 4 cm to about 7.5 cm, more preferably from about 5 cm to about 6 cm, even more preferably about 5.5 cm. The width of the tampon 26 measured from one edge 26D to the other is preferably between about 2 cm and about 7 cm, more preferably from about 3 cm to about 5 cm, even more preferably about 3 cm to about 4 cm.

Caliper (or thickness) measurements given herein were measured using an AMES gage with a 0.25 psi (1.7 kPa) (gauge) load and a 0.96 inch (2.44 cm) diameter foot. Those skilled in the art will recognize that if a 0.96 inch (2.44 cm) diameter foot is not appropriate for a particular sample size, the foot size may be varied while the load on the gauge is accordingly varied to maintain a confining pressure of 0.25 psi (1.7 kPa) (gauge). The caliper of the tampon 26 is preferably in the range of from about 2 mm to about 8 mm, more preferably from about 3 mm to about 6 mm.

The tampon 26 may also be constructed in the shape of an oven mitt, balloon, or light bulb such as shown in FIG. 2. In such an embodiment, the widest portion of the tampon 26 is near the head 26A, and is designated $W_H$. In the embodiment shown in FIG. 2, $W_H$ may preferably be in range of from about 1.5 cm to about 8 cm, more preferably from about 4 to about 6 cm. The tampon 26 is narrower at the trailing end 26B. The width at the trailing end 26B is designated as $W_B$ in FIG. 2. Preferably, this $W_B$ is in the range of from about 1 cm to about 3 cm, more preferably about 2.5 cm.

The tampon 26 may be constructed from a wide variety of liquid-absorbing materials commonly used in absorbent articles such as rayon, cotton, or comminuted wood pulp which is generally referred to as airfelt. Examples of other suitable materials include creped cellulose wadding; coform structures; meltblown polymers; chemically stiffened, modified or cross-linked cellulosic fibers; synthetic fibers such as crimped polyester fibers; peat moss; tissue including tissue wraps and tissue laminates; or any equivalent material or combinations of materials, or mixtures of these. Preferred absorbent materials comprise cotton (including needle punched cotton), rayon (including tri-lobal and conventional rayon fibers, needle punched rayon), folded tissues, synthetic and/or natural fibers. The tampon 26 may comprise a single substance or a combination of substances. Additionally, superabsorbent materials, such as superabsorbent polymers or absorbent gelling materials may be incorporated into the tampon 26.

In the preferred embodiment shown in FIG. 1, the tampon 26 is formed using a soft absorbent material such as rayon, cotton (either long fiber cotton or cotton linters) or other suitable natural or synthetic fibers or sheeting. The materials for the tampon 26 can be formed into a fabric, web, or batt that is suitable for use in the tampon 26 by any suitable process. Suitable types of absorbent structures include woven fabrics, nonwoven fabrics, including needle punched nonwoven fabrics, hydro entangled structures, chemically entangled structures, felted structures, and other types of absorbent structures. Needle punched fabrics are particularly suitable if it is desirable to provide the tampon 26 with a textured outside surface. The tampon 26 may include osmotically swelling materials.

One non-limiting example of a simplified manner of constructing the tampon 26 is as follows. In this example, the tampon 26 is made from materials similar to those currently used in conventional tampons (e.g. rayon or cotton or a blend thereof). A rectangular web of absorbent material similar to that used to form a tampon pledget for conventional compressed tampons can be used as a starting structure. This web of absorbent material can be of any suitable thickness that is capable of being formed into a bag that is conformable as described herein. A preferred thickness range for such a web is about one-half of the range given above for the preferred ranges of the overall caliper of the completed tampon 26.

As noted, a wide variety of materials and structures are suitable from which to construct the tampon 26 of the present invention. Such a tampon may have a wide variety of such properties as density, basis weight, and the like. For example, a tampon 26 of the present invention may be constructed from a web of rayon and cotton (such as that used in conventional tampons) having a basis weight of about 165 $g/m^2$. Another suitable example is a web of chemically entangled cotton having a basis weight of about 180 $g/m^2$. Needle punched rayon (such as a tri-lobal rayon) or needle punched cotton may also be formed into a suitable web.

The web of absorbent material is then preferably covered with a single thin layer of overwrap material. The overwrap may be made of any suitable material and serves to help prevent fibers from the tampon 26 from coming loose in the wearer's body. It should be noted that not all materials and structures from which the tampon 26 may be made will require the use of an overwrap. For example, when a needle punched or hydroentangled web is used to form the tampon 26, an overwrap is not always needed and is preferably dispensed with. Nevertheless, tampons both with and without an overwrap structure are within the scope of the present invention.

A preferred material for the overwrap is rayon, although other materials including those made from bicomponent fibers, or other natural or synthetic fibers, may also be suitable. The overwrap is folded around the faces of the web of absorbent material. The overwrap is preferably of a sufficient size such that it extends beyond the ends of the web of absorbent material. The portions of the overwrap that extend beyond the ends of the web are preferably sealed together. The wrapped web of absorbent material is then folded about itself into a tube shape (or flattened tube shaped) and sealed with a seam along one side and at one end to form the wrapped web of absorbent material into a bag structure. If desired, the bag can be turned inside out so the seams will be on the inside of the bag structure.

In alternative embodiments, two webs may be used which are then sealed together in any suitable manner. Such techniques include stitching, ultrasonically bonding, gluing with adhesives, or any other suitable means known in the art. Two webs may be joined along two seams which may be located along the side edges 26D of the tampon 26. Construction of a tampon 26 of the present invention from two webs of material joined in the manner indicated may be more convenient when the tampon 26 will have a non regular overall shape such as that shown in FIG. 2. It is not necessary that tampon 26 be sealed along the entire side edge 26D of the tampon 26 to form the bag-like structure of the present invention. The tampon 26 may have a bag like, upper portion (the portion toward the head 26A of the tampon) and have more open "flaps" (that is, unsealed portions) toward the lower portion of the tampon 26.

The tampon 26 of the present invention may also be formed by winding webs of absorbent material such as those described above into a tube structure.

Figure 3:
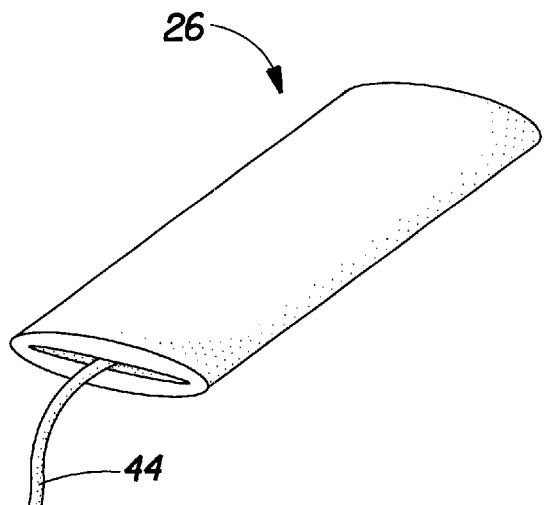
FIG. 3 shows the tampon of FIG. 1 in a flattened configuration.

The tampon 26 shown in FIG. 1 is highly conformable and flaccid. In this preferred embodiment, the tampon 26 has little to no resiliency. In other words the tampon 26 shown in FIG. 1 will tend to remain in its collapsed "bag like" state when not subjected to any external forces. The tampon 26 should have little tendency to "spring" to any particular opened state or shape. The tampon 26 may have a shape modulus of compression, i.e. the unidirectional pounds force required to deform the tampon 26 to its collapsed state, i.e. collapsed so any interior cavity is substantially eliminated and the interior surface is reduced to line contact between opposing points such as shown in FIG. 3, below 0.05 pounds.

The tampon 26 of the present invention because of its unique design (and through the use of the unique applicator discussed below) may be made of materials not previously utilized for a dry expanding, substantially non-resilient tampon. Previous dry-expanding tampons, such as those shown in U.S. Pat. No. 3,749,094 issued to Duncan and U.S. Pat. Nos. 3,794,029 and 3,766,921 both issued to Dulle. These and similar attempts at producing a dry-expanding tampon focused on the use of absorbent foam due to its resiliency. The tampon 26 of the present invention need not, and preferably, does not incorporate foam as the primary absorbent material of the tampon.

One advantage of the tampon 26 of the present invention is because of its highly effective shape and lack of fiber compression, less overall absorbent material need be used than in convention tampons. Only about half of the absorbent material found in a conventional tampon of the highly compressed type need be used in the tampon 26 of the present invention in order to obtain an overall absorbency of 6–9 grams in standard syngyna testing. In preferred embodiments, the overall absorbency of the tampon 26 ranges from about 5 to about 30 grams in standard syngyna testing. It will be appreciated by one skilled in the art that the overall absorbency may be varied as desired by the type and amount of absorbent used.

Figure 4:
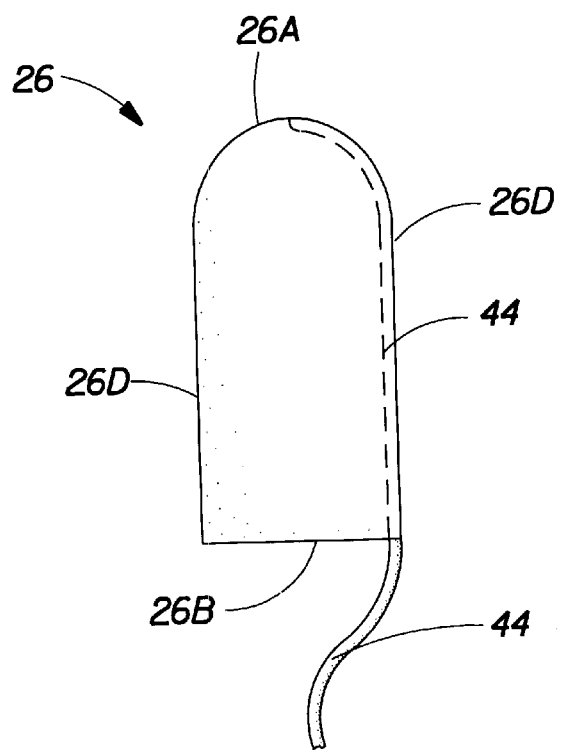
FIG. 4 is a front view of a tampon of the present invention in which the withdrawal cord is attached along one side edge of the tampon.

The tampon 26 preferably has a removal mechanism such as removal string 44 that is attached thereto. Other removal elements may include a tape, ring, loop, or like structure. The removal string 44 can be attached to the inside surface 42 or the outside surface 40 of the tampon 26. The removal string 44 may be attached generally down the center of one surface 26C of the tampon 26 (as shown in FIG. 1), or the removal string 44 may be attached generally along one of the edges 26D of the tampon 26 as shown in FIG. 4. In one particularly preferred tampon (shown in FIG. 10 and discussed further below), the removal string 44 is attached to the inside surface of the tampon 26, adjacent to the head 26A of the tampon 26 to facilitate inversion of the tampon 26 upon removal.

Figure 7:
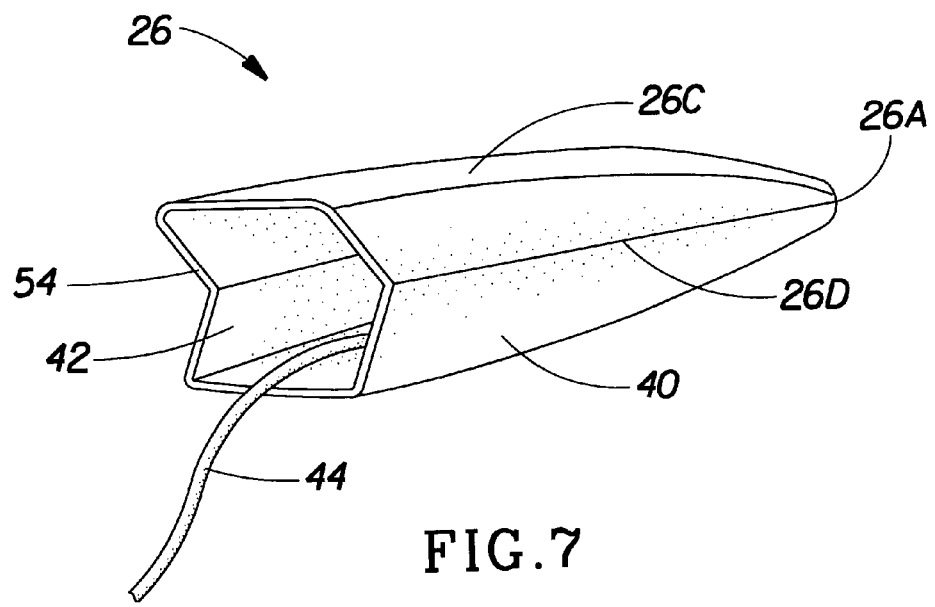
FIG. 7 shows an embodiment of the tampon of the present invention in which the sides of the tampon are pleated.
Figure 7A:
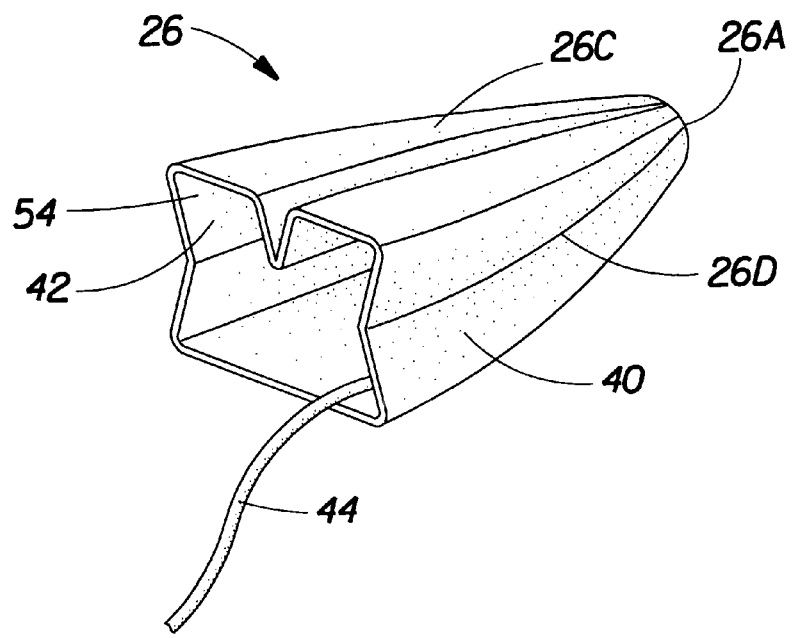
FIG. 7A shows an embodiment of the tampon of the present invention in which the sides of the tampon show pleated folds.
Figure 7B:
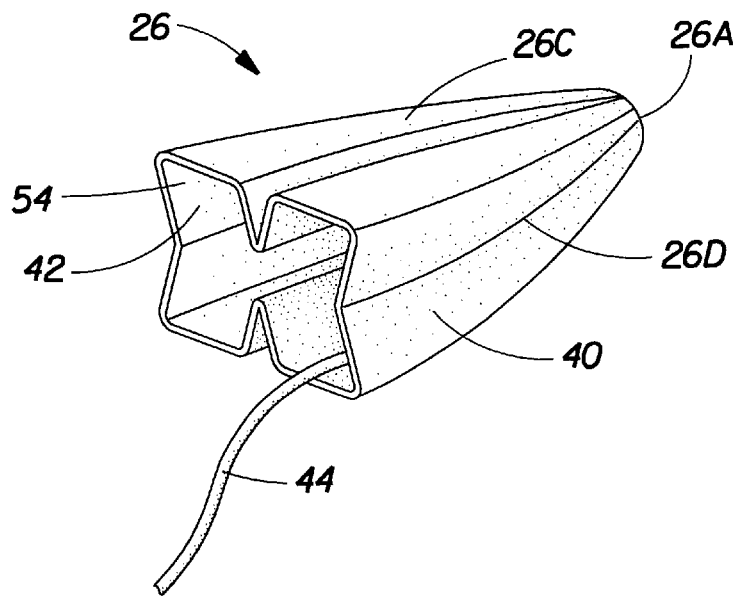
FIG. 7B shows an embodiment of the tampon of the present invention in which the sides of the tampon show pleated folds.

As shown in FIG. 7, the tampon 26 may have a cross section in which two of its sides are pleated so that it resembles a paper shopping bag when looking into the open end of the tampon 26. The pleats 54 will allow the sides of the tampon 26 to expand laterally. In another variation on the embodiment shown in FIG. 7, the tampon 26 may be provided with a plurality of pleats 54 disposed around its crosssection that are capable of opening in any desired direction. The tampon 26 may also be provided with a plurality of pleats across its major flat surfaces 26C such that it tends to expand laterally in a manner similar to an accordion. The pleats 54 in the tampon 26 also may improve its ability to conform to the shape of the vaginal cavity, which is often described as having an "H-shaped" cross-section. A pleated tampon 26 such as that shown in FIG. 7 is advantageously made from a tampon originally having a shape similar to that shown in FIG. 2. The wider head portion of the tampon 26 of FIG. 2 is tucked inward to form a pleated tampon 26 such as that shown in FIG. 7.

Figure 5:
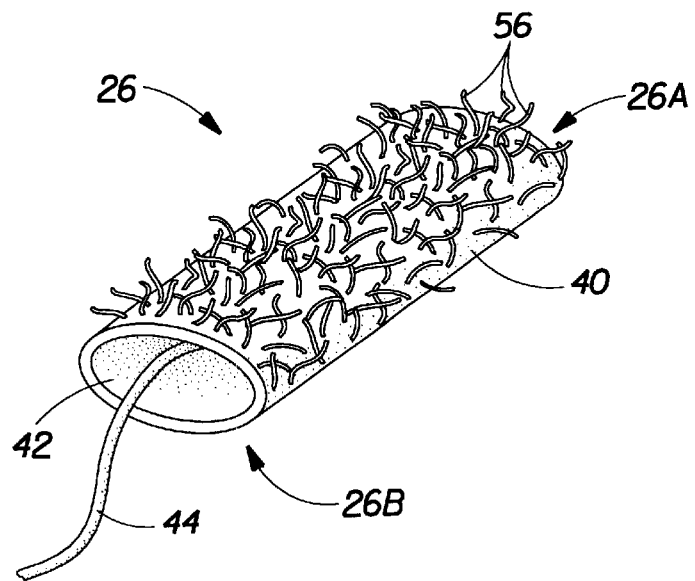
FIG. 5 shows an embodiment of the tampon of the present invention in which the outer surface of the tampon is provided with texturing elements.

The outside surface 40 of the tampon 26 may be plain, or it can be textured. Preferably, it is textured. An example of such a textured outer surface 40 is shown in FIG. 5. The texturing can take the form of texturing fibers 56 as shown in FIG. 5. Texturing may be provided by needle punching the outside surface 40 of the tampon 26. Additionally, the texturing fibers 56 may be attached to the outer surface of the tampon 26 or may be attached to the interior of the tampon and pass through it. The texturing fibers 56 may be attached to an intermediate location between the inside and outside surfaces of the tampon 26 or any combination of these locations. The texturing fibers 56 may comprise microfibrils or conventional fibers of the type used for the surface of the tampon 26 or fibers of a different type.

The tampon 26 preferably has an outside surface 40 which comprises a plush or terry cloth type fabric which has a plurality of texturing fibers 56 or other texturing elements extending outwardly therefrom. The texturing fibers 56 may be randomly oriented or may be aligned in a particular direction or directions. Preferably these texturing elements are generally perpendicular to the surfaces of the expanded tampon 26. This is in contrast to current tampons in which the fibers generally lay flat relative to the surface of the expanded tampon. These texturing fibers 56 or other texturing elements penetrate into the rugosites in the vaginal cavity to intercept menses and reduce "by-pass" failures (failures from menses traveling in these rugosites and around the tampon). Preferably, the texturing fibers 56 or other texturing elements may have a tendency to flex and/or orient themselves in response to forces exerted by the vaginal surfaces.

The texturing fibers 56 or other texturing elements may be "looped" and attached to the surface of the tampon 26 at both ends. Suitable texturing elements may be formed from a single long fiber or a series of fibers which are punched in and out of the surface of the tampon 26 to form a plurality of loops. In some embodiments, both the outside surface 40 and the inside surface of the tampon 26 may be provided with texturing elements such as texturing fibers 56. A textured surface on the interior of the tampon 26 will help to transfer fluid from one side of the bags' absorbent surface to the other side of the absorbent surface so that the full capacity of the tampon 26 is most effectively used. Interior texturing elements are also useful when the tampon 26 is inverted upon removal, as more fully discussed below. The texturing elements may also take the form of "tufts" or protuberances extending from the otherwise planar surface of the tampon 26. The texturing elements may be in the form of ridges and valleys imparted to the surface of the tampon 26.

The texturing fibers 56 or other texturing elements are preferably hydrophilic so as to facilitate the ready transfer of fluid from the vaginal surfaces to the tampon 26. The texturing fibers 56 or other texturing elements may also be configured to transfer fluid from the vaginal surfaces to the tampon 26 through the use of a density gradient, hydrophilicity gradients, an osmotic driving force, surface energy gradient, capilarity, or a similar mechanism. Suitable materials for use in the fluid acquisition/transfer complex 30 are rayon (including, e.g., conventional, tri-lobed or multi-lobed rayon fibers), polyethylene, polypropylene, polyester, synthetic bicomponent fibers, absorbent foams and combinations thereof, all of which fibers may be used either singly or in combination with other fibers are known in the art. Capillary channel fibers are a highly preferred fiber for the microfibrils 56.

Figure 6:
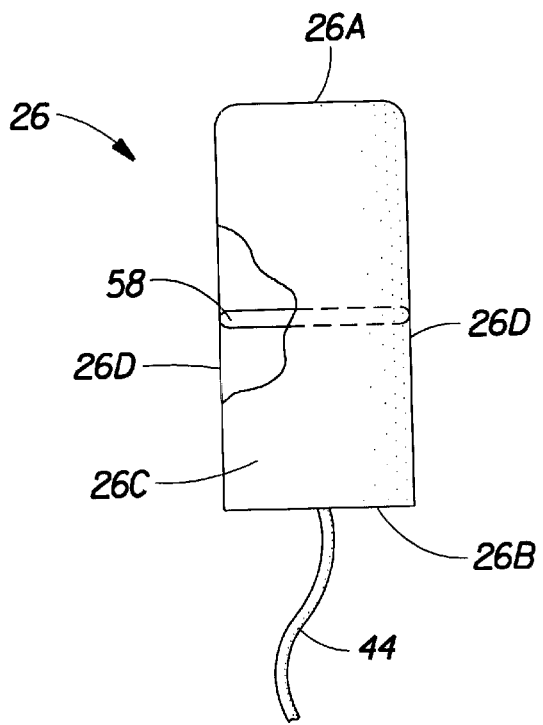
FIG. 6 shows an embodiment of the tampon of the present invention in which the tampon is provided with an internal annular ring.

In the embodiment shown in FIG. 6, the tampon 26 is provided with an annular ring 58 which assists it in expanding to contact the vaginal surfaces. The tampon 26 may also be also be constructed such that it is generally cylindrical or circular in cross-section, without a major surface. In other words, in contrast to the tampon 26 shown in FIG. 1, in alternative embodiments, the tampon may be non-directional in terms of a tendency to flatten in a particular plane or direction. Such a feature allows the tampon 26 to be inserted in any orientation without losing its ability to expand effectively in the lateral direction once inserted. This is particularly helpful when the tampon is inserted digitally or with a non-directional inserter.

The tampon 26 of the present invention need not be completely hollow in its interior portion. In the embodiment shown in FIG. 8, the tampon 26 comprises an interior projection 78 inside of the main "bag" portion. This interior projection 78 is preferably constructed from absorbent materials and may be highly compresses absorbent material. When the interior projection 78 is comprised of a compressed absorbent material, it may be thought of as a "little tampon" within the overall highly conformable bag structure which comprises the overall tampon 26. The interior projection 78 is preferably attached to on the inside surface of the head 26A of the tampon 26.

The interior projection 78 may add some initial stiffness to the head 26A of the tampon to assist in digital insertion or insertion with a push-rod type applicator. The flacidity of the main portion of the tampon 26 will allow it to be spread laterally following insertion, while the stability provided by the interior projection 78 acts as an aid to insertion. The interior projection 78 may also be used to increase the capacity of the tampon 26 and may be used for ultimate storage of absorbed fluid. In other words the outer surface of the tampon 26 may be constructed of a hydrophilic material which transports fluid toward the interior projection 78 for ultimate storage thorough the use of capillary action, density gradients or other similar mechanism.

Figure 8:
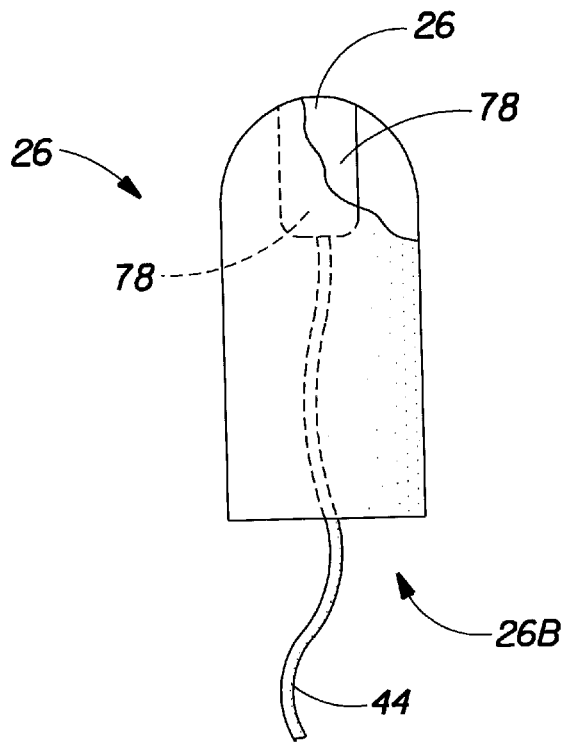
FIG. 8 shows an embodiment of the tampon of the present invention in which the interior of the tampon contains an interior projection.

An insertion aid similar to that described above with respect to the interior projection 78 shown in FIG. 8, may also be provided in the form of a interior resilient member. The resilient member may be located in the head potion 26A of the tampon 26. The resilient member may comprise any suitable material, including an absorbent material such as a resilient sponge, or foam or may be non-absorbent such as polyurethane The resilient member assists in the insertion of the flaccid tampon 26 and may also act to assist in its spreading once deployed within the vagina.

Figure 9:
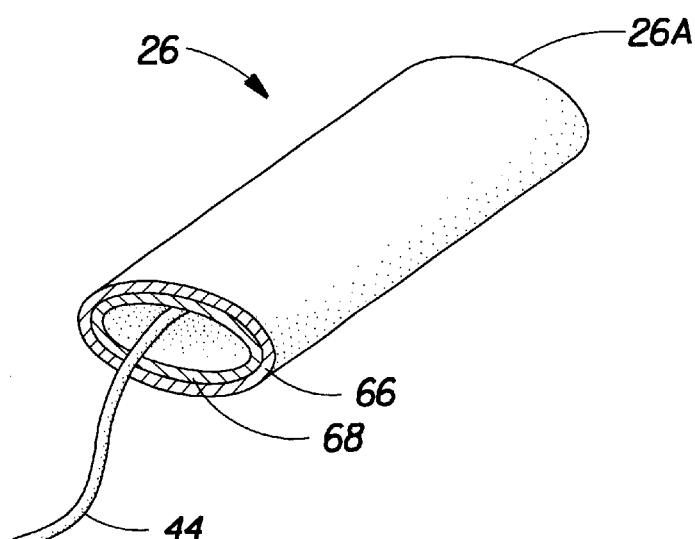
FIG. 9 shows an embodiment of the tampon of the present invention in which the tampon has a layered structure.

It has been found during development of the present invention, that the tampon 26 may be constructed from multiple materials. These materials may be blends of materials, or they may be layered throughout the tampon 26. FIG. 9 shows an embodiment of the present invention in which the tampon 26 is constructed of an outer layer 66 and an inner layer 68. As noted above, two preferred materials for the tampon 26 are rayon and cotton.

Rayon is a preferred material for use in tampons because of its high fluid absorption rate. Additionally, rayon is highly compressible and has a high fluid capacity on a gram per gram basis. One disadvantage with rayon, however, is that it tends to release previously absorbed fluid when subjected to an external confining pressure. This phenomenon, sometimes referred to as compression failure or "squeeze out," is discussed further in U.S. Pat. No. 3,749,094. The forces exerted on the tampon by the wearer's body movements or muscle contraction may lead to compression failure.

Cotton conventionally used in tampons typically has a lower fluid acquisition rate than rayon and also typically has a lower absorbent capacity than rayon a gram per gram basis. Nevertheless, cotton is a preferred material for use in tampons because of its superior ability to retain acquired fluid when subjected to external confining pressures.

The benefits of both rayon and cotton may be combined by constructing the tampon 26 with a layered structure as shown in FIG. 9. In the embodiment shown in FIG. 9, the outer layer 66 is comprised primarily of rayon, and the inner layer 68 is comprised primarily of cotton. In variations on this embodiments, the tampon 26 may be constructed of a single layer comprising a blend of such materials, such as a 50%/50% homogenous blend of rayon and cotton. Multiple layers of such blends may also be employed. The layers may be in the form of an airlaid nonwoven web, a carded web, or other suitable web or batt of material.

The embodiment shown in FIG. 9 may also comprise a liquid impervious barrier located between the inner layer 68 and the outer layer 66. Alternatively, such a liquid impervious barrier may line the inner surface of the tampon 26.

Figure 10:
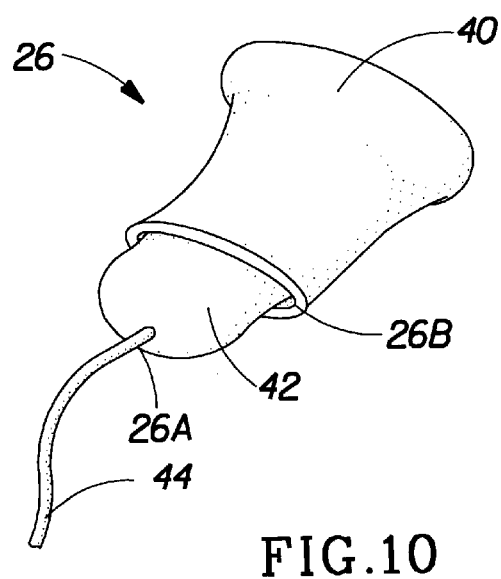
FIG. 10 shows the inversion of a tampon of the present invention during removal with the withdrawal string.

The rayon and cotton layered structure described above allows the tampon to quickly absorb fluid through the action of the rayon layer. The interior layer of cotton is then highly effective for retention of stored fluid. This structure is particularly effective when the tampon 26 is inverted upon removal as shown in FIG. 10. When the tampon is turned inside out for removal as shown in FIG. 10, the cotton will be the body contacting layer. As such, it will tend to retain the absorbed fluid as the tampon is withdrawn through the vaginal introitus and squeezed by the pubo-coxis muscles.

If the tampon 26 is provided with a liquid impervious barrier between the inner layer 68 and 66, when the tampon 26 is inverted as shown in FIG. 10, the layer contacting the body upon withdrawal will be a clean absorbent surface. This provides a "wiping" action which tends to absorb any remaining fluid from the vaginal surfaces as the tampon 26 is withdrawn.

The interior layer 68 of the tampon 26 shown in FIG. 9 may also be provided with a different texture than the outer layer 66. The outer layer 66 may be provided with the microfibrils 56 described above and shown in FIG. 5, while the inner layer 68 is provided with a smooth texture. This allows for good vaginal contact and absorption during use, combined with a comfortable and smooth withdrawal when the tampon 26 is optionally inverted for removal. The inner surface 42 of the tampon 26 may comprise a material that has a lower coefficient of friction against the wearer's body than the outside surface. The inside surface 42 can also be provided with other features, such as a cleansing or lubricating composition that can clean the wearer's vaginal area when the tampon 26 is removed. Similarly, the outside surface 40 of the tampon 26 may be provided with a lubricant to facilitate the insertion of the tampon 26 (especially digital insertion).

Figure 11:
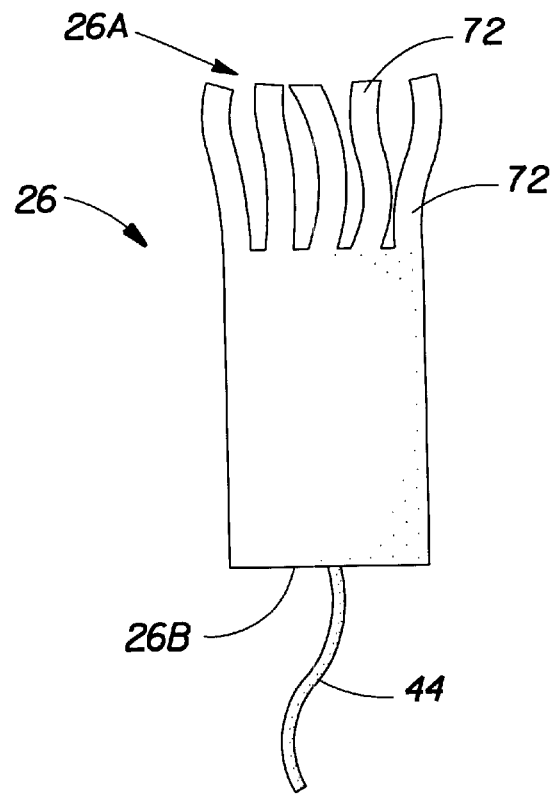
FIG. 11 shows an embodiment of the tampon of the present invention in which the tampon has tufts or fingers at the insertion end.

In addition to texturing fibers 56 or other texturing elements, the tampon 26 may be provided with larger structures such as "tufts" or "fingers" to further engage the ruggi. Examples of such "tufts" or "fingers" are shown in FIG. 11. The tufts or fingers 72 should be flexible and capable of independent movement relative to the main body of the tampon 26. In this manner they will tend to spread more or less randomly, and be held in by natural adhesion to the vaginal surfaces in their spreadout configuration. The tufts or fingers 72 may preferably be provided with a density gradient, hydrophilicity gradient, or similar mechanism to direct fluid toward the surface and interior of the tampon 26.

Figure 13:
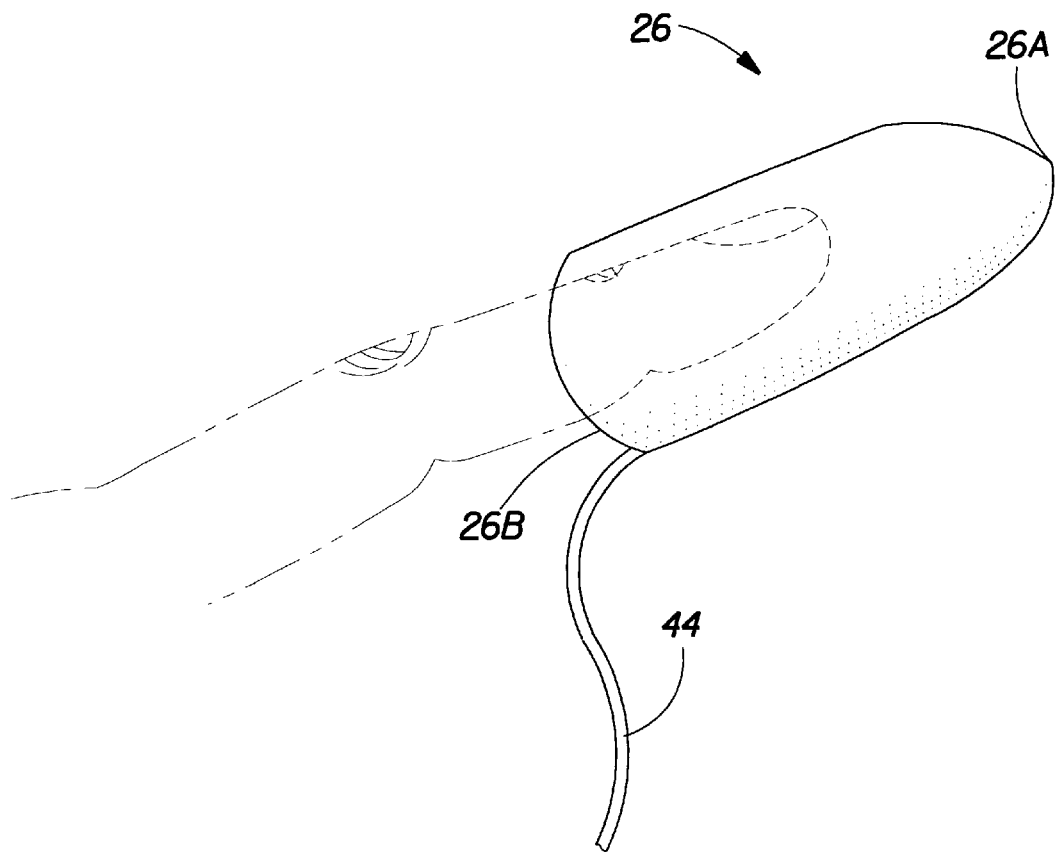
FIG. 13 shows digital insertion of the tampon of the present invention.

The tampon 26 of the present invention is designed to be inserted digitally (as shown in FIG. 13) or through the use of a unique applicator 20. Because the tampon 26 preferably has a hollow interior, the user may insert her finger within the tampon 26 to facilitate insertion and spreading. The tampon 26 is designed to reside "lower" in the vaginal canal than more highly compressed conventional tampons which contributes to their comfort and effectiveness at covering the entire vaginal surface. The tampon 26 of the type shown in FIG. 8 is especially effective for digital insertion because the interior projection 78 provides a surface against which to insert the tampon 26. Additionally, although the tampon 26 is designed to reside "lower" in the vaginal canal than conventional tampons, the interior projection 78 may assist some users (such as those with small fingers) in achieving an acceptable depth of insertion for maximum product effectiveness.

Figure 12:
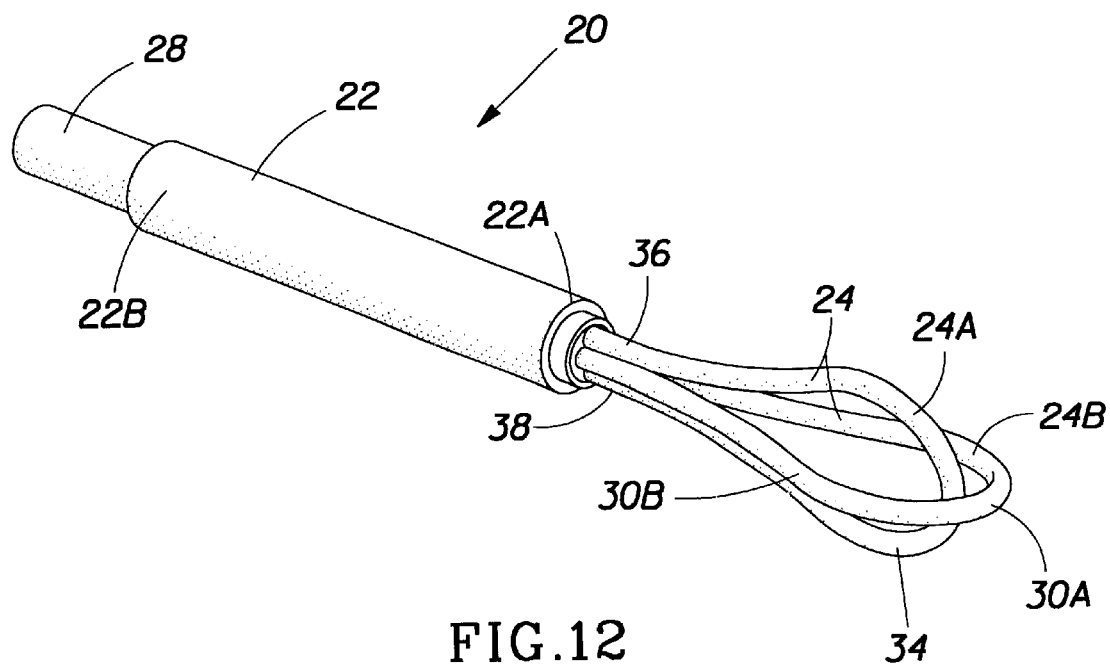
FIG. 12 shows a perspective view of a unique applicator for insertion of the tampon of the present invention.

In addition to digital insertion, the tampon 26 of the present invention may also be inserted with a unique applicator 20 an embodiment of which is shown in FIG. 12. The applicator 20 shown in FIG. 12 is an example of a simplified version of one embodiment of the unique applicator designed to be used with tampons of the present invention. The tampon applicator 20 shown in FIG. 12 generally comprises a holder in the form of a tube, preferably an elongate tube 22 and at least one flexible, movable structure that is adapted to reside inside the tube 22 until it is pushed out the end of the tube. The flexible, movable structure comprises flexible loop 24. The flexible loop 24 comprises the applicator element in such an embodiment. The tampon 26, fits over the loop 24 and is capable of expanding when the loop 24 expands. As shown in FIG. 12, the tampon applicator 20 preferably also includes a plunger 28 for expelling the tampon 26. The plunger 28 is telescopically and slidably mounted inside the elongate tube 22. The applicator 20 is preferably inexpensive enough to manufacture that it can be disposable after a single use, although it is also possible for the applicator 20 to be reusable.

The holder 22 is preferably an elongate hollow tube that has insertion end (or "expulsion end") 22A, a gripping end 22B. The holder 22 can be of either the open end type, or the closed end type. The holder 22 can be constructed similarly to tubular holders of the type used in tampon applicators currently in use. Examples of such a tubular holder are described in U.S. Pat. No. 5,346,468 issued to Campion, et al. on Sep. 13, 1994, and U.S. Pat. No. 5,558,631 issued to Campion, et al. on Sep. 24, 1996. The holder 22 can be of any suitable cross-sectional shape. Suitable cross-sectional shapes include, but are not limited to circular, oval, racetrack, flattened circular, and elliptical. Preferably, the holder 22 has a circular cross-sectional configuration.

If the holder 22 is of a closed end type, the "petals" that define the opening at the insertion end can be of any conventional type. It has been found that it is not necessary to modify the shape of the opening at the insertion end to permit the flexible loop 24 to be pushed through the opening, since the petals are sufficiently flexible to move out of the way of the flexible loop 24. The opening may have a cruciform shape.

The flexible, movable structure 24 can comprise any suitable type of flexible, expandable, and preferably rounded element that is capable of remaining in the holder 22 until it is desired to deploy the tampon. When the time to deploy the tampon 26 arises, the flexible, movable structure 24 is capable of moving within the holder 22 (hence it is movable) and expanding to spread the tampon 26 within the vaginal cavity.

The flexible, movable structure 24 is preferably in the form of a loop so that it is most comfortable when it is deployed. The flexible, movable structure 24 preferably has a relatively low force of expansion (force which it applies to objects in contact with it when it opens) so that it minimizes any distortion of the vaginal opening when the tampon 26 is inserted through the vaginal opening, and minimizes the distortion of the vaginal cavity when the tampon 26 is deployed within the vaginal cavity. While the force of expansion is preferably relatively low, it should be sufficient to spread the tampon over the surface of the vagina. The flexible, movable structure 24 preferably only distorts the vaginal cavity to the extent necessary to properly deploy the tampon 26 therein. The flexible, movable structure 24 is also capable of flexing to adjust to the shape of the vaginal cavity. This can be contrasted with devices that use structures employing hinged arms in order to expand.

The flexible loop 24 preferably comprises an elongate piece of material 34 such as a flexible rod or tube, having two ends 36 and 38 that extend in the same general direction. The flexible loop 24 may also be referred to herein as a "wisk" since it resembles a wisk of the type used for cooking (e.g., for beating eggs). (However, the loops on such a cooking implement are typically not flexible and expandable). The piece of material 34 that comprises the flexible loop has one portion which is formed into the flexible and expandable loop 24. The flexible loop is advantageous in that all of the portions that will come into contact with the wearer's body are preferably convexly rounded to provide a comfortable structure for contacting the wearer's body, in contrast to prior devices having angular hingetype mechanisms. However, it is also possible to modify the flexible loop 24 to provide one or more portions thereof with one or more segments along its length that are concavely rounded, rectilinear, or both.

Thus, not only is the leading end 30A of the flexible loop 24 convexly rounded, but the longitudinal sides 30B of the flexible loop 24 are also preferably convexly rounded. In some embodiments, the entirety of the longitudinal sides 30B of the flexible loop 24 is convexly rounded. The fact that the longitudinal sides 30B are convexly rounded causes them to be biased outward away from each other when the flexible loop 24 is constrained in width, such as when it resides in the holder 22. As a result, the flexible loop 24 expands on its own when it is pushed out of the end of the holder 22, and no mechanical mechanism is required to be present in the applicator 20 to spread the flexible loop 24.

The piece of material 34 that is formed into the flexible loop 24 can comprise any suitable material that has the characteristics described herein. The piece of material (or rod) 34 can have any suitable cross-sectional shape. Preferably, it has a round cross-sectional shape. The piece of material 34 should preferably be very comfortable when it comes in contact with the delicate parts of the user's body. The piece of material 34 is preferably resiliently elastomeric so that it does not undergo "set" when it is within the holder 22 and can expand when outside the holder 22. The piece of material 34 should preferably be substantially non-creeping. Preferred materials for the piece of material 34 typically comprise some type of rubber, such as natural rubber, latex, nitrile, polyurethane, and silicon rubbers.

The flexible loop 24 is movable within the tubular holder 22, and is preferably slidably mounted within the tubular holder 22. The flexible loop 24 has an initial width which is less than or equal to the inside diameter of the tubular holder 22, and a deployed width which is greater than the inside diameter of the tubular holder 22. That is, the flexible loop 24 expands from a first transverse width to a second transverse width. In one non-limiting example, the flexible loop 24 may have an initial width of about 7/16 inch (about 1 cm) and a deployed width of about 1 inch (about 2.5 cm) to about 1 1/4 inches (about 3 cm).

The applicator 20 preferably comprises two (or more) loops of material. The loops of material 24 can be oriented in any suitable relationship relative to each other. In this particularly preferred embodiment, the loops of material 24A and 24B are preferably oriented at an angle of about 90 degrees relative to each other when the applicator 20 is viewed from the end. This embodiment has the advantage of providing an increased likelihood of ensuring that at least one of the loops of material will be oriented in the same plane as the vaginal cavity regardless of the orientation of the applicator 20 when it is inserted in the vaginal cavity. In the embodiment shown in FIG. 12, even though the loops 24A and 24B were initially oriented at right angles, they should be sufficiently flexible under low forces that one of the loops (such as 24A) will be capable of "flattening" and adjusting its orientation to that of the other loop. This allows it to conform to the collapsed orientation of the vaginal cavity. The applicator 20 is capable of adjusting in this manner regardless of how the loops are initially oriented relative to the vaginal cavity. As a result, there is no need for the user to be concerned with properly orienting the applicator 20 relative to the vaginal opening.

The plunger 28 comprises a component that is used to expel the tampon 26 from its position within the holder 22 when the plunger 28 is pushed manually into the holder 22. The plunger 28 can be any type of component that is suitable for this purpose. The plunger 28 can be constructed similarly to plungers of the type used in tampon applicators currently in use. An example of a suitable plunger is described in U.S. Pat. No. 5,346,468 issued to Campion, et al. on Sep. 13, 1994, and U.S. Pat. No. 5,558,631 issued to Campion, et al. on Sep. 24, 1996.

It should also be understood that the plunger 28 is an optional, but preferred component for use with the applicator 20, and that the applicator 20 will be fully functional if the plunger 28 is omitted, or if the plunger 28 comprises a part of the loops 24. The applicator 20 may be of the conventional type, or may be a compact type applicator.

To use the tampon applicator of the present invention the user will typically hold the holder 22 in one hand at the finger grips on the same. The user holds the end of the plunger 28, such as with her thumb and forefinger, and pushes the plunger 28 inward to slide the plunger 28 within the holder 22. The user pushes on the plunger 28 until the loops 24 open and the tampon 26 is deployed. The user then pulls the plunger 28 back outward in order retract the loops 24, and removes the applicator 20 from the vaginal opening.

The combination of the applicator 20 and the tampons 26 described herein provides numerous advantages. One particular advantage is that the applicator 20 described herein is capable of applying a force to the inside of the lead end or "head" of the tampons of the type described herein. That is, it applies a force against the portion of the tampon that is oriented toward the wearer's cervix. The applicator 20 is also capable of expanding the lead end of these tampons. Thus, the applicator 20 of the present invention is able to fully deploy the bag-like tampons described herein, unlike prior spreading tampon applicators in which the greatest expansion occurs at some intermediate portion along the length of the applicator. Of course, alternative embodiments of the tampon 26 can be constructed which are configured so that the applicators described herein provide the greatest expansion at an intermediate portion of the tampon. For example, if the bag like tampons described herein are provided with an insert (such as shown in FIG. 8) inside thereof at the head end 26A of the tampon 26, the applicators 20 described herein may press on the end of such a small compressed tampon rather than the head end of the bag like structure. As a result, the greatest expansion may occur at some intermediate portion of the bag like tampon. In other embodiments, the applicators described herein can be used or modified to provide the greatest expansion at the trailing end of the tampon.

In view of the foregoing, it is therefore possible for the applicators 20 described herein to contact and apply a force to the inside surface of the head of the tampon. This force preferably has a laterally oriented vector component. This will ensure that the tampon 26 is able to be expanded to a maximum width dimension at the head of the tampon 26. Alternatively, the applicators 20 can apply a force to a portion that is on the inside of the tampon 26 that is midway (or half way) from the trailing end 26B of the tampon 26 to the head 26A of the tampon, or to some such portion that lies between the midpoint of the tampon and the head 26A of the tampon. In other embodiments, the applicators 20 can apply a force to a portion that is on the inside of the tampon 26 that is one third of the way from the trailing end 26B of the tampon 26 to the head 26A of the tampon, or to some such portion that lies between a point which lies between a point which is one-third of the way between the trailing end 26B of the tampon 26 and the head 26A of the tampon and the head 26A of the tampon.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

The disclosures of all patents and patent applications referred to in this specification are hereby incorporated by reference as if fully set forth herein. While particular embodiments of the present invention have been illustrated and described, it would be obvious to those skilled in the art that various other changes and modifications can be made without departing from the spirit and scope of the invention.

What is claimed is:

1. A catamenial tampon comprising: a bag-like conformable absorbent body, said tampon having an outer surface, an inner surface, a head portion and a trailing portion, said inner surface of said tampon defining an interior of said tampon wherein said head portion is closed and said trailing portion defines an opening into said interior of said tampon, and wherein said tampon comprises texturing elements adapted to penetrate into the rugosities in the vaginal cavity, wherein said texturing elements are disposed on said outer surface of said tampon and extending outwardly therefrom wherein said texturing elements have a lower density than said outer surface of said tampon such that a density gradient is created from said texturing elements to said outer surface.

2. The tampon of claim 1 wherein said texturing elements comprise texturing fibers.

3. The tampon of claim 1 wherein said texturing elements are hydrophilic.

4. The tampon of claim 1 wherein said texturing elements comprise capillary channel fibers.

5. A catamenial tampon comprising: a bag-like conformable absorbent body, said tampon having an outer surface, an inner surface, a head portion and a trailing portion, said inner surface of said tampon defining an interior of said tampon wherein said head portion is closed and said trailing portion defines an opening into said interior of said tampon, wherein when compressed in a flat configuration said outer surface has a maximum width which is located intermediate said head portion and said trailing portion wherein said maximum width exceeds the width of said trailing portion.

6. The tampon of claim 5 wherein when collapsed in a flat configuration, said tampon has a generally balloon-shaped plan view.

7. The tampon of claim 5 wherein said tampon has a syngyna absorbency of from about 5 to about 30 grams.

8. The tampon of claim 6 wherein said tampon has a syngyna absorbency of from about 5 to about 20 grams.

9. A catamenial tampon comprising: a bag-like conformable absorbent body, said tampon having an outer surface, an inner surface, an outer layer, an inner layer, a head portion and a trailing portion, said inner surface of said tampon defining an interior of said tampon wherein said head portion is closed and said trailing portion defines an opening into said interior of said tampon, wherein said absorbent body comprises a layered structure such that the material composition of said outer surface differs from the material composition of said inner surface, and wherein at least a portion of said outer layer defines said outer surface and wherein at least a portion of said inner layer defines said inner surface, said inner layer having a higher density than said outer layer.

10. The tampon of claim 9 wherein said tampon comprises at least an outer layer and an inner layer wherein at least a portion of said outer layer defines said outer surface and wherein at least a portion of said inner layer defines said inner surface.

11. The tampon of claim 10 wherein said inner surface comprises a liquid impervious barrier.

12. The tampon of claim 10 wherein said inner layer has a higher density than said outer layer.

13. The tampon of claim 10 wherein said inner layer comprises primarily cotton.

14. The tampon of claim 10 wherein said outer layer comprises primarily rayon.

* * * * *